(12) United States Patent
Etter

(10) Patent No.: US 6,761,909 B1
(45) Date of Patent: Jul. 13, 2004

(54) PARTICULATE INSULIN-CONTAINING PRODUCTS AND METHOD OF MANUFACTURE

(75) Inventor: Jeffrey B. Etter, Boulder, CO (US)

(73) Assignee: RxKinetix, Inc., Louisville, CO (US)

(*) Notice: Subject to any disclaimer, the term of this patent is extended or adjusted under 35 U.S.C. 154(b) by 0 days.

(21) Appl. No.: 09/469,733

(22) Filed: Dec. 21, 1999

(51) Int. Cl.$^7$ .......................... A61K 9/14; A01N 25/02; C07K 14/62

(52) U.S. Cl. .......................... 424/489; 424/43; 424/45; 424/499; 424/400; 424/501; 514/2; 514/3; 530/303; 530/350; 530/304; 530/418; 426/425; 426/426; 426/330

(58) Field of Search .............................. 424/489, 499, 424/43, 45, 400, 501, 44–48, 490, 497; 514/2, 3, 4, 12; 530/303, 350, 304, 418; 426/425, 426, 330

(56) References Cited

U.S. PATENT DOCUMENTS

| | | | |
|---|---|---|---|
| 4,895,719 A | | 1/1990 | Radhakrishnan et al. ...... 424/45 |
| 5,460,173 A | * | 10/1995 | Mulhauser et al. ..... 128/203.15 |
| 5,503,869 A | | 4/1996 | Van Oort .................... 427/2.14 |
| 5,619,984 A | | 4/1997 | Hodson et al. ......... 128/203.15 |
| 5,639,441 A | * | 6/1997 | Sievers ........................ 424/9.3 |
| 5,654,007 A | | 8/1997 | Johnson et al. .............. 424/489 |
| 5,770,559 A | * | 6/1998 | Manning et al. ................ 514/2 |
| 5,794,613 A | | 8/1998 | Piskorski ................ 128/203.12 |
| 5,795,594 A | | 8/1998 | York ........................... 424/489 |
| 5,814,678 A | | 9/1998 | Randolph ..................... 522/18 |
| 5,851,453 A | | 12/1998 | Hanna et al. ................... 264/5 |
| 5,874,064 A | * | 2/1999 | Edwards ....................... 424/46 |
| 5,875,776 A | | 3/1999 | Vaghefi ................. 128/203.15 |
| 5,997,848 A | * | 12/1999 | Patton ......................... 424/46 |
| 6,063,910 A | * | 5/2000 | Debenedetti et al. ....... 530/418 |
| 6,177,103 B1 | * | 1/2001 | Pace et al. ................... 424/489 |
| 6,372,260 B1 | * | 4/2002 | Andersson et al. .......... 424/501 |

FOREIGN PATENT DOCUMENTS

| | | |
|---|---|---|
| EP | 0 069 715 B1 | 11/1986 |
| EP | 0 542 314 A1 | 5/1993 |
| EP | 0 542 314 B1 | 1/1998 |
| WO | WO 95/01221 | 1/1995 |
| WO | WO 96/00610 | 1/1996 |
| WO | WO 96/32149 | 10/1996 |
| WO | WO 98/04308 | 2/1998 |
| WO | WO 98/29141 | 7/1998 |
| WO | WO 98/36825 | 8/1998 |
| WO | WO 99/16419 | 4/1999 |
| WO | WO 99/59710 | 11/1999 |

OTHER PUBLICATIONS

Yeo et al., "Formation of Microparticulate Protein Powders Using a Supercritical Fluid Antisolvent" Biotechnology and Bioengineering, vol. 41, pp 341–346, 1993.*

Winters et al., "Precipitation of Proteins in Supercritical Carbon Dioxide" Journal of Pharmaceutical Sciences, vol. 85, No. 6, pp 586–594, Jun. 1996.*

"Drug Formulation Technology For Compounds Administered by Inhalation," Alliance Pharmaceutical Corp; Web Page www.allp.com/PulmoSpheres/PS_WHITE.HTM; publication date unknown.

Zia, Hossein et al., "Comparison of Nasal Insulin Powders Prepared by Supercritical Fluid and Freeze–Drying Techniques," *Particulate Science and Technology*, 15:273–301 (1997).

Knutson, Barbara L. et al., "Preparation of Microparticulates Using supercritical Fluids,"*Drugs Pharm. Sci.*, 77:89–125 (1996).

Tom, Jean W. and Pablo G. Debenedetti, "Formation of Bioerodible Polymeric Microspheres and Microparticles by Rapid Expansion of Supercritical Solutions," *Biotechnol. Prog.*, 1991, vol. 7, No. 5, pp. 403–411.

Winters, Michael A. et al., "Long–Term and High–Temperature Storage of Supercritically–Processed Microparticulate Protein Powders," *Pharm. Res.*, vol. 14, No. 10, 1997, pp. 1370–1378.

Winters, Michael A. et al., "Precipitation of Proteins in Supercritical Carbon Dioxide," *J. Pharmaceutical Sciences*, vol. 85, No. 6, Jun. 1996, pp. 586–594.

Yeo, Sang–Do et al., "Secondary Structure Characterization of Microparticulate Insulin Powders," *J. of Pharmaceutical Sciences*, vol. 83, No. 12, Dec. 1994, pp. 1651–1656.

Yeo, Sando–Do et al., "Formation of Microparticulate Protein Powders Using a Supercritical Fluid Antisolvent," *Biotechnology and Bioengineering*, vol. 41, No. 3, Feb. 5, 1993, pp. 341–346.

* cited by examiner

Primary Examiner—Karen Cochrane Carlson
Assistant Examiner—Samuel Wei Liu
(74) Attorney, Agent, or Firm—Marsh Fischmann & Breyfogle LLP

(57) ABSTRACT

Provided is a compressed anti-solvent technique for manufacture of insulin-containing powders for pulmonary delivery. The insulin is processed in a cosolvent system including two or more mutually soluble organic solvents. Also provided are powders manufacturable by the manufacture method, including powders of substantially pure insulin and powders including a biocompatible polymer for pulmonary sustained insulin release applications. Also provided are packaged products including insulin-containing powder in a container that is receivable by and operable with a dry powder inhaler to produce an aerosol including dispersed insulin-containing particles when the inhaler is actuated.

55 Claims, 3 Drawing Sheets

US 6,761,909 B1

PARTICULATE INSULIN-CONTAINING PRODUCTS AND METHOD OF MANUFACTURE

FIELD OF THE INVENTION

The invention involves particulate insulin-containing products useful for pulmonary delivery applications, manufacture of insulin-containing particles using compressed anti-solvent precipitation, inhalers actuatable to produce aerosols including insulin-containing particles. In one aspect, the insulin-containing particles are multi-component particulate particles including insulin and a biocompatible polymer useful for sustained release applications.

BACKGROUND OF THE INVENTION

Recently, there has been significant interest in pulmonary delivery of a variety of drugs to subjects via inhalation of aerosolized drug powders.

One important consideration for pulmonary delivery is that small particles in a narrow range of aerodynamic diameters of from about 1 micron to about 5 microns appear to be most effective for deposition in the lungs in a manner to contribute to drug delivery. Larger particles tend to become lodged in the throat during inhalation and smaller particles tend to be exhaled without depositing in the lungs. Because it is difficult to manufacture powder batches restricted to the desired particle size, significant losses of drugs are often experienced during administration to a subject, due to the presence of large quantities of excessively large and/or excessively small particles. Another important consideration is that handling the drug micro-powders during dose measurement and packaging is difficult, because of the small size and often cohesive nature of the particles. Significant quantities of powder can be lost during these handling operations. Significant powder losses can also occur during aerosolization of the powder to produce an aerosol for inhalation by a subject. For example, a dry powder inhaler is typically used to aerosolize a dry powder for inhalation. Significant powder losses in a dry powder inhaler can be caused by poor dispersability of the powder due to interparticulate cohesive forces and by particles coating interior surfaces of the inhaler. The cumulative losses can be large due to combined losses from powder handling, aerosolization and less than optimum particle size and size distribution characteristics. Moreover, if the powder has poor dispersability characteristics, then the aerosol may include a significant quantity of large aggregates that are too large for effective deposition in the lungs. The result is that often only a small percentage of a batch of powder originally manufactured for pulmonary delivery is ultimately delivered to the lungs of a subject. Some of these losses can be reduced through careful design of handling operations and careful design of inhalers to promote satisfactory aerosolization. Losses could further be reduced, however, through manufacture of powders having improved particle size and size distribution characteristics, improved flowability for ease of handling and/or improved dispersability for ease of aerosolization.

One drug that has received considerable attention for pulmonary delivery is insulin. Techniques that have been proposed for preparing insulin powders for pulmonary delivery include spray drying, solvent extraction and jet milling of lyophilized insulin. One problem with spray drying, however, is that the insulin is subjected to high temperatures, which can significantly degrade the insulin and may impair its activity. With solvent extraction techniques, there are often significant problems associated with contamination of powders by residual solvents and surfactants used during the manufacturing operation. The presence of these residual contaminants is undesirable. Jet milling can damage the biological activity of the insulin. Also, the characteristics of powders produced by spray drying, solvent extraction and jet milling could be improved to reduce losses during powder handling and aerosolization and to improve delivery of the aerosolized powder to a subject's lungs.

Another method that has been proposed for manufacturing insulin powders is to precipitate insulin from solution by contacting the solution with an anti-solvent fluid under supercritical conditions. Some references discussing supercritical anti-solvent precipitation of insulin include: Yeo, Sang-Do, et al., "Formation of Microparticulate Protein Powders Using a Supercritical Fluid Antisolvent," Biotechnology and Bioengineering, Vol. 41, pp. 341–346 (1993); Yeo, Sang-Do, et al., "Secondary Structure Characterization of Microparticulate Insulin Powders," J. Pharmaceutical Sciences, Vol. 83, No. 12, pp. 1651–1656 (1994); Winters, Michael A., et al., "Precipitation of Proteins in Supercritical Carbon Dioxide," J. Pharmaceutical Sciences, Vol. 85, No. 6, pp. 586–594 (1996); Winters, Michael A., et al., "Long-Term and High-Temperature Storage of Supercritically-Processed Microparticulate Protein Powders," Pharmaceutical Research, Vol. 14, No. 10, pp. 1370–1378 (1997); and European Patent No. 0 542 314.

The supercritical anti-solvent precipitation technique has the advantages of producing insulin powders with very little, if any, residual solvent contamination without subjecting the insulin to a high temperature. The noted references, however, are primarily focused on supercritical anti-solvent precipitation of insulin powders for use in applications other than pulmonary delivery, such as subcutaneous applications, and do not discuss processing techniques specifically designed to produce powders with characteristics that are advantageous for pulmonary delivery applications.

There is a significant need for improved techniques to prepare insulin powders for pulmonary delivery applications and for insulin powders with improved powder characteristics for pulmonary delivery applications.

SUMMARY OF THE INVENTION

With the present invention, it has been found that powders often having improved characteristics for pulmonary delivery applications are manufacturable by compressed anti-solvent precipitation when the insulin is processed in a feed solution including the insulin in a cosolvent system including two or more mutually soluble organic solvents.

Therefore, in one aspect the present invention provides a method of making insulin-containing powders in which a feed solution including the insulin in such a cosolvent system is contacted with a compressed anti-solvent fluid, typically compressed carbon dioxide in a near critical or supercritical state, to precipitate insulin-containing particles that are then separated from the anti-solvent fluid. The cosolvent system includes at least a first organic solvent and a second organic solvent, although additional organic solvents may be included as desired for a particular application. The first organic in the cosolvent system is typically a significantly better solvent for insulin and the second organic solvent typically significantly enhances processing to promote preparation of high quality powders for pulmonary delivery applications. As a further possible refinement, it is typically preferred that the cosolvent system include less than about 50% by weight of the first organic solvent.

It has been found that prior supercritical anti-solvent techniques that describe use of a single solvent system for insulin manufacture, typically either DMSO or DMFA as the sole solvent, do not produce powders with sufficiently good flowability or dispersability characteristics to be advantageous for pulmonary delivery. Processing according to the method of the present invention, however, often results in significantly enhanced flowability and/or dispersability of the powders. As a possible refinement on the present invention, it has further been found that the cosolvent system should preferably be substantially organic in nature, meaning that it should be substantially free of water. Although at first blush it might seem that the presence of some water in the cosolvent system would stabilize the insulin during processing, it has been found that the presence of water in the cosolvent system is highly detrimental to flowability and/or dispersability characteristics of the manufactured powder.

With the manufacture method of the present invention, the specific mutually soluble organic solvents preferred for inclusion in the cosolvent system will depend upon the specific composition and/or other characteristics of insulin-containing particles to be manufactured. In one embodiment, substantially pure insulin particles are manufactured. In that case, examples of some preferred cosolvent systems include DMSO as the first organic solvent and a lower alcohol, such as methanol, ethanol or isopropanol, as the second organic solvent. In another embodiment, multi-component particles are manufactured that include both insulin and a biocompatible polymer as an expient for sustained release of insulin. To manufacture such multi-component particles for sustained release, examples of some preferred cosolvent systems include a lower alcohol, such as methanol, ethanol or isopropanol, as the first organic solvent and methylene chloride as the second organic solvent, with the cosolvent system optionally being acidified with a small concentration of an inorganic acid, such as hydrochloric acid. The manufacture of sustained release powders suitable for pulmonary delivery is a particularly significant aspect of the present invention.

In another aspect, the present invention provides insulin-containing powder useful for pulmonary delivery of insulin. These powders are manufacturable by the method of the present invention and typically have desirable flowability and/or dispersability characteristics for pulmonary delivery. In one embodiment, the powder includes substantially pure insulin. In another embodiment, the powder includes multi-component particles with insulin and a biocompatible polymer for sustained release of insulin. Particularly noteworthy with respect to the multi-component powders is that they can be made to have a high degree of insulin encapsulation, which promotes a prolonged release of insulin following administration to a subject. Although the degree of encapsulation can be varied depending upon the specific requirements for a particular application, in most cases, the degree of insulin encapsulation will be at least 30%, and will frequently be much higher. For many applications, the degree of insulin encapsulation will be 70% or more. The degree of insulin encapsulation provides an indication as to the sustained release characteristics of a powder, with a higher degree of insulin encapsulation generally corresponding with a lower level of insulin burst. A high degree of insulin encapsulation is often achievable with the present invention even when the insulin load in the multi-component particles is high. For example, high degrees of insulin encapsulation have been achieved with insulin loading of 25 weight percent, and even 50 weight percent insulin in the powder. Furthermore, the multi-component particles, as manufactured, are typically in the form or rather large aggregates of small primary particles, which are typically smaller than about 5 microns and more typically significantly smaller. These aggregates can be broken up, however to facilitate preparation of an aerosol with dispersed insulin-containing particles having a mass median aerodynamic diameter in a desired size range of from about 1 micron to about 5 microns. This breaking up of the aggregates is often achievable when the powder is aerosolized in a dry powder inhaler due only to the force exerted on the powder during the aerosolization. This is particularly advantageous, because aggregate particles will tend to be easier to handle. Alternatively, the aggregates can be broken up prior to aerosolization, such as by jet milling. The powders, in the aggregate form and as broken up are within the scope of the present invention.

In yet another aspect, the present invention provides a packaged powder product including powder of the present invention contained in a container that is receivable by and operable with an inhaler, typically a dry powder inhaler, so that when the inhaler is actuated the powder is removed from the container and aerosolized to produce an aerosol including dispersed insulin particles for inhalation by a subject for pulmonary delivery. In a preferred embodiment, the container includes a plurality of compartments, each including an insulin-containing powder batch including a unit dose of insulin, such that each successive actuation of the inhaler aerosolizes a different powder batch to provide an aerosol with a single dose of insulin when inhaled by a subject.

These and other aspects of the present invention will be more fully appreciated based on the detailed disclosure provided below.

DETAILED DESCRIPTION OF THE INVENTION

In one aspect, the present invention involves an anti-solvent precipitation process for manufacturing insulin-containing powders designed specifically for pulmonary delivery applications. It has been found that powders having advantageous properties for pulmonary delivery applications can be prepared by contacting a liquid feed containing insulin with a compressed anti-solvent fluid, wherein the liquid feed includes a certain type of cosolvent system.

Figure 1:
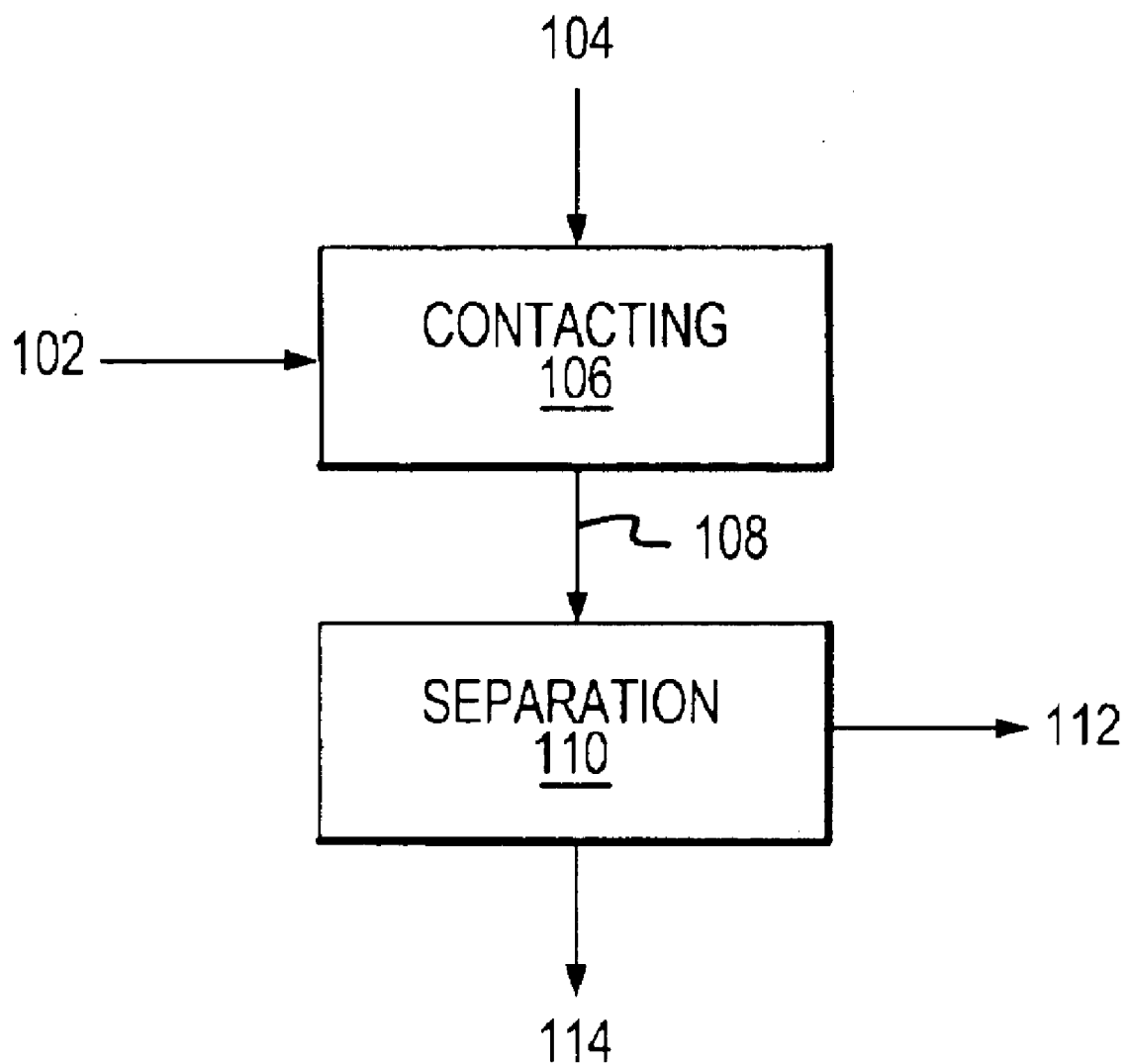
FIG. 1 is a block flow diagram of one embodiment of compressed anti-solvent processing of the present invention for manufacture of insulin-containing powders.

Referring to FIG. 1, a simplified process flow diagram shows general processing involved with one embodiment of the anti-solvent precipitation method of the present invention for manufacturing insulin-containing powders. As shown in FIG. 1, a feed solution (102) including insulin, and a compressed anti-solvent feed (104) are contacted in a contacting step (106) to form insulin-containing particles as the anti-solvent feed (104) invades and expands the feed solution (102). The contacting step (106) results in a mixture (108) of process fluids and particles containing insulin. The resulting mixture (108) is then subjected to a solid/liquid separation (110) to recover an insulin-containing particulate product (112). Process fluid (114) remaining after the separation step (110) includes anti-solvent fluid from the anti-solvent feed (104) and solvents removed from the feed solution (102) during the contacting step (106). The contacting step (106) and the separation step (110) are shown as two separate steps, but it will be appreciated that these steps could be conducted as separate operations in separate process apparatus, or could be conducted as a combined operation in a single process apparatus.

The compressed anti-solvent feed (104) includes a compressed anti-solvent fluid having a strong solvating power for solvents in the feed solution (102), and in which insulin should be no more than slightly soluble. Any material may be used as the anti-solvent fluid that is suitable for processing under the specific operating conditions contemplated. Preferably, the insulin being processed should be essentially insoluble in the compressed anti-solvent fluid. Nonlimiting examples of materials that may be used as the compressed anti-solvent fluid include one or more of carbon dioxide, ethane, ethylene, nitrous oxide, fluoroform ($CHF_3$), dimethyl ether, propane, butane, isobutane, propylene, chlorotrifuoro-methane ($CClF_3$), sulfur hexafluoride ($SF_6$), bromotrifluoromethane ($CBrF_3$), chlorodifluoromethane ($CHClF_2$), hexafluoroethane, carbon tetrafluoride, monofluoromethane, 1,1-difluoroethylene and ammonia. Particularly preferred for use as the compressed anti-solvent fluid is carbon dioxide. Also, it is preferred that the anti-solvent feed consist essentially of the compressed anti-solvent fluid.

The anti-solvent feed (104) is typically in a near critical or supercritical state when contacted with the feed solution (102) during the contacting step (106), and the contacting step (106) is conducted in a pressurized vessel, at the desired temperature and pressure. The contacting step (106) is typically conducted at a reduced temperature of larger than about 0.90, and preferably larger than about 0.95, calculated relative to the critical temperature of the anti-solvent fluids. Although the temperature during the contacting step (106) may be as high as desired, so long as not significantly detrimental to the insulin, the contacting step (106) will typically be conducted at a reduced temperature in a range having an upper limit of about 1.10, and more preferably about 1.05, as calculated relative to the critical temperature of the anti-solvent fluid. The reduced temperature of a fluid is the ratio of the temperature of the fluid to the critical temperature of the fluid, with the temperatures in the ratio being expressed in K. For carbon dioxide, the critical temperature is 31° C. (304 K). Therefore, for carbon dioxide, a reduced temperature in a preferred range of from about 0.95 to about 1.05 translates to a preferred operating temperature range during the contacting step (106) of from about 16° C. (188 K) to about 46° C. (319 K). Also, the contacting step (106) is typically conducted at a reduced pressure of larger than about 0.5, preferably larger than about 0.8, and more preferably larger than about 0.9, calculated relative to the critical pressure of the anti-solvent fluids. Although the pressure during the contacting step (106) may be as high as desired, so long as not significantly detrimental to the insulin, the contacting step will typically be conducted at a reduced pressure in a range having an upper limit of about 2, and preferably about 1.5, relative to the critical pressure of the anti-solvent fluid. The reduced pressure of a fluid is the ratio of the pressure of the fluid to the critical pressure of the fluid. For carbon dioxide, the critical pressure is 72.9 atmospheres. Therefore, for carbon dioxide, a reduced pressure in a preferred range of from about 0.9 to about 1.5 translates to an operating pressure range during the contacting step (106) of from about 66 atmospheres to about 109 atmospheres. In many instances, the contacting step will be performed under supercritical conditions, meaning that the reduced temperature for the anti-solvent fluid is greater than 1 (in which case the reduced temperature will also necessarily be greater than 1).

The separation step (110) may involve any suitable technique for separating the insulin-containing particles from process fluids to produce the insulin-containing particulate product (112) and the process fluids (114). Examples of suitable separation techniques include sedimentation, filtration and centrifuging. Filtration is a generally preferred technique for the separation step (110).

As noted previously, with the manufacture method of the present invention, the feed solution (102) comprises a cosolvent system including the insulin. The insulin will typically be in the form of a true solution in the cosolvent system. In some applications, however, some or all of the insulin may be suspended in a colloidal state in the cosolvent system. Therefore, as described herein, the "feed solution" includes the situation when some or all of the insulin is dissolved in the cosolvent system in a true solution (i.e., dispersion of insulin in the cosolvent system at a molecular level) and includes the situation when some or all of the insulin is in the state of a "colloidal solution" (i.e., dispersion of the colloidal-sized insulin domains suspended in and dispersed throughout the cosolvent system). Furthermore, when it is said herein that insulin-containing particles are "precipitated," such precipitation includes the situation when some or all of the insulin, or some or all of some other component to be included in the particles, comes out of a true solution to form the particles, as well as the situation when the cosolvent system is removed from a colloidal suspension of insulin, to form insulin-containing particles no longer trapped as a dispersed colloidal phase in the cosolvent system.

According to the present invention, the cosolvent system includes two or more different organic solvents that are mutually soluble in the proportions used and at the temperature and pressure conditions existing during the contacting step (106), and that are also preferably mutually soluble at ambient conditions of temperature and pressure. It has been found that manufacture using the cosolvent system according to the invention often produces insulin-containing powders that have improved characteristics for use in pulmonary delivery applications. The specific solvents used in the cosolvent system will depend upon the particular application, as discussed more fully below. For most applications, however, a first organic solvent will be a significantly better solvent for insulin and another organic solvent will be a significantly worse solvent for insulin. The first organic solvent and the second organic solvent may be present in the cosolvent system in any proportion suitable for processing under the desired conditions. For most applications, the cosolvent system is preferably richer in the second organic solvent than in the first organic solvent. The proportion of the first organic solvent must, however, be present in an adequately high quantity to solubilize the insulin at a sufficiently high concentration for processing into the desired insulin-containing particles. Typically, the weight ratio of the second organic solvent to the first organic solvent in the cosolvent system is in a range having a lower limit of about 10:90, preferably about 30:70 and more preferably about 50:50 and having an upper limit of about 99:1, preferably about 90:10 and more preferably about 80:20. Particularly preferred is for the weight ratio of the second organic solvent to the first organic solvent to be in a range of from about 50:50 to about 80:20. The concentration of insulin dissolved in the cosolvent system will depend upon the specific powder to be manufactured, but will typically be in a range of from about 0.1 to about 5 mg of insulin per milliliter of the cosolvent system, with concentrations of smaller than about 3 mg of insulin per milliliter of the cosolvent system being generally preferred for most applications.

An important consideration for selecting solvents for inclusion in the cosolvent system is the composition of the particular insulin-containing powder to be made. In that regard the insulin-containing powder may include substantially only insulin, or may include one or more other components in addition to insulin. A preferred multi-component powder includes insulin together with a biocompatible polymer, preferably in a form that significantly prolongs release of insulin following pulmonary delivery to subject.

In one preferred embodiment of the manufacture process of the present invention, the insulin-containing powder includes substantially only insulin. When preparing single component powders of substantially pure insulin, the cosolvent system will typically include at least a first organic solvent that is a significantly better solvent for insulin and a second organic solvent that is a significantly worse solvent for insulin, and with the second organic solvent preferably being more readily extractable by the anti-solvent feed (104) than the first organic solvent. The first organic solvent may be any solvent in which insulin is sufficiently soluble and that is at least reasonably extractable by the anti-solvent feed (104). Examples of organic solvents for use as the first organic solvent in this embodiment include dimethyl sulfoxide (DMSO), dimethyl formamide (DMFA) and lower alcohols (especially $C_1$–$C_5$ alkanols) such as methanol and ethanol. DMSO is particularly preferred for use as the first organic solvent to make substantially pure insulin powders. When using a lower alcohol, such as methanol or ethanol, or when using DMFA as the first organic solvent, it is typically desirable to add a small amount of acid, such as hydrochloric acid, to the first organic solvent to enhance the solubility of insulin.

When making substantially pure insulin powders, the second organic solvent may be any organic solvent that is miscible with the first organic solvent under the operating conditions of the contracting step (106) and that is readily extractable by the anti-solvent feed (104). In a preferred embodiment, the second organic solvent is more readily extractable by the anti-solvent feed (104) than the first organic solvent. By being more readily extractable, it is meant that the second organic solvent is more quickly invaded and expanded by the anti-solvent feed (104) under the conditions present during the contacting step (106). Typically, organic solvents that have a higher volatility are more readily extractable by the anti-solvent feed (104). Therefore, the second organic solvent will typically be a more volatile solvent than the first organic solvent. Examples of groups of organic liquids that may be used as the second organic solvent include various alcohols, ketones, aldehydes, nitriles, and halogenated hydrocarbons, and particularly lower molecular weight members of these groups that are readily extractable by the anti-solvent feed (104). Particularly preferred for use as the second organic solvent are lower molecular weight alcohols, and even more particularly preferred are C1–C5 alkanols, which will typically be monohydric, and may be primary, secondary or tertiary alcohols. Examples of particularly preferred alcohols include methanol, ethanol, propanols (including isopropanol and n-propanol), butanols and pentanols. Most preferred for use as the second organic solvent are methanol, ethanol and isopropanol.

Solvents such as DMSO and DMFA, which are useful as the first organic solvent with the present invention, have previously been identified in the literature as solvents in which insulin may be dissolved for anti-solvent precipitation to prepare insulin powders. It has been found with the present invention, however, that the use of either DMSO or DMFA alone is typically problematic. For example, solutions of insulin in either DMSO or DMFA tend to be very viscous and difficult to process. Furthermore, insulin powders prepared using only DMSO or DMFA as a solvent tend to not be free flowing, and are often sticky and therefore difficult to handle and disperse. With the present invention, however, it is been found that the problems associated with the use of only DMSO or DMFA can largely be avoided by using the cosolvent system, resulting in feed solutions that are easier to process and manufactured insulin-containing powders that are more likely to be free flowing. Free-flowing powers are particularly preferred for use in pulmonary delivery applications, because free flowing powders tend to be easier to handle, to be easier to disperse during aerosolization, and to produce higher quality aerosols for delivery of insulin to a subject's lungs.

In another preferred embodiment of the manufacture process of the present invention, multi-component powders are prepared including insulin and a biocompatible polymer. Other components may also be included in these multi-component powders, if desired. Multi-component powders including insulin and a biocompatible polymer are typically intended for sustained release of insulin when administered by pulmonary delivery. A significant aspect of this embodiment of the present invention is that the multi-component powders may be made with a high degree of encapsulation of the insulin by the biocompatible polymer. This result is particularly surprising, because previous experience of the inventors has indicated that it is very difficult to obtain a high degree of encapsulation of insulin.

In this embodiment, both the insulin and the biocompatible polymer are typically included in the cosolvent system. Some or all of the insulin and/or the biocompatible polymer can be dissolved in the cosolvent system, to form a true solution, or may be in the form of a colloidal dispersion in the cosolvent system. Preferably, however, at least the biocompatible polymer will be dissolved in the cosolvent system. The cosolvent system will typically include a first organic solvent that is a better solvent for insulin and a second organic solvent that is a better solvent for the biocompatible polymer. The biocompatible polymer is typically biodegradable and is also typically hydrophobic. Examples of biocompatible polymers useful with the present invention include repeating units representative of polymerizing at least one of the following: an alphahydroxycarboxylic acid, a cyclic diester of an alphahydroxycarboxylic acid, a dioxanone, a lactone, a cyclic carbonate, a cyclic oxalate, an epoxide, and a glycol. Preferred biocompatible polymers comprise at least some repeating units representative of polymerizing at least one of lactic acid, glycolic acid, lactide, glycolide, ethylene oxide and ethylene glycol. Other examples of biocompatible polymers include poloxamers (polyethoxy-polypropoxy triblock copolymers), polyanhydrides, and phosphatriazenes. Polyanhydrides are copolymers typically of a bis(p-carboxyphenoxy) alkane (typically $C_3$–$C_6$ alkanes) and dicarboxylic acid (such as sebacic acid or fumaric acid). Phosphatriazenes are copolymers typically made by reacting a polychlorophosphazene with various nucleophiles in various ratios. Specific examples of phosphotriazenes include poly(p-methylphenoxy-imidazole) phosphazene and poly (ethylglycinato)(p-methylphenoxy) phosphazene. The biocompatible polymer may be of any desired molecular weight that is soluble in the cosolvent system. Generally preferred molecular weights are in a range of from about 2 kDa to about 300 kDa, and preferably of from about 20 kDa to about 150 kDa. Furthermore, preferred biocompatible polymers are biodegradable, meaning that the matrix of the polymer will degrade over time after administration to a subject. Hydrolytic degradation is a common degradation mechanism for preferred biocompatible polymers.

A particularly preferred biocompatible polymer for use with the present invention is poly(lactic acid). As used herein, poly(lactic acid) means polymers having repeating units

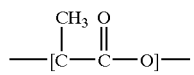

regardless of the monomer from which the repeating units are derived. For example, as used herein, poly(lactic acid) includes polymers made by condensation polymerization of lactic acid as a monomer as well as by ring-opening polymerization of lactide as a monomer. Furthermore, the poly (lactic acid) may be poly (L-lactic acid), poly (D-lactic acid) or poly (D,L-lactic acid). Although any desired molecular weight of poly(lactic acid) may be used that is soluble in the cosolvent system, preferred molecular weights for use with the present invention are in a range of from about 2 kDa to about 300 kDa, with molecular weights of from about 20 kDa to about 150 kDa being more preferred.

The biocompatible polymer and the insulin may be included in any desired proportions. Typically, the weight ratio of the insulin to the biocompatible polymer will be in a range of having a lower limit of about 1:99, preferably about 5:95 and more preferably about 10:90 and having an upper limit of about 99:1, preferably about 65:35, more preferably about 50:50 and even more preferably about 35:65. Particularly preferred for most applications is a weight ratio range of from about 10:90 to about 35:65.

As noted previously, when making the multi-component particles including a biocompatible polymer, the first organic solvent is typically a better solvent for the insulin and the second organic solvent is typically a better solvent for the biocompatible polymer. Furthermore, the first organic solvent is typically a poor solvent for the biocompatible polymer and the second organic solvent is typically a poor solvent for insulin. Also, because the biocompatible polymer is typically hydrophobic, the second organic solvent is typically a non-polar solvent. Conversely, the first organic solvent is typically a polar solvent. The solubility of insulin in the first organic solvent is often at least an order of magnitude larger than the solubility of the biocompatible polymer in the first organic solvent, and the solubility of the biocompatible polymer in the second organic solvent is often at least an order of magnitude larger than the solubility of insulin in the second organic solvent. Examples of solvents useful as the first organic solvent include DMSO, DMFA, alcohols, and more preferred are lower molecular weight alcohols, and particularly C1–C5 alkanols. Particularly preferred are methanol, ethanol, propanols (including n-propanol and iso-propanol), butanols, and pentanols; with methanol, ethanol and iso-propanol being even more preferred. When DMFA or alcohols are used as the first organic solvent, they will often be acidified, such as with a small quantity of HCl, to improve the solubility of the insulin in the cosolvent system.

Examples of solvents useful as the second organic solvent when making multi-component particles include methylene chloride, formaldehyde, dioxolane, chloroforn, benzene, ethyl ether, toluene, xylene, 1,3-dioxane and tetrahydrofuran (THF). Certain second organic solvents will generally be more preferred for use with different biocompatible polymers. For example, preferred second organic solvents include: 1) for poloxamers-methylene chloride, chloroform, THF and 1,3-dioxane; 2) for polyanhydrides-methylene chloride, chloroform, benzene, ethyl ether, toluene, xylene, THF and 1,3-dioxane; 3) for phosphatriazenes-THF, chloroform, 1,3-dioxane and methylene chloride; and 4) for poly(lactic acids)-methylene chloride, formaldehyde, dioxolane and chloroform. Especially preferred as the second organic solvent for most applications, and especially for use with poly(lactic acids), is methylene chloride.

The cosolvent system may include one or more solvents in addition to the first organic solvent and the second organic solvent. As one example, the cosolvent system could include DMSO and a C1–C5 alkanol (which together solubilize the insulin) and methylene chloride (to solubilize the biocompatible polymer). Furthermore, the cosolvent system may include more than one biocompatible polymer, with the cosolvent system being chosen to solubilize all of the different biocompatible polymers being used.

As will be appreciated, the solubility of insulin in lower molecular weight alcohols, such as methanol, ethanol and iso-propanol is not great. It has been found, however, that the solubility of insulin is sufficiently high in those alcohols for manufacture of the multi-component particles including the biocompatible polymer, although it is often necessary to slightly acidify alcohols to attain the desired level of insulin solubilities. The multi-component particles typically include a larger fraction of the biocompatible polymer than the insulin, and the somewhat limited solubility of insulin in the listed alcohols is generally not a problem, especially when the alcohols are slightly acidified. In one embodiment, a small amount of acid, typically an inorganic acid, and preferably hydrochloric acid, is included in the cosolvent system to provide the acidification. The presence of the acid increases the solubility of the insulin in the cosolvent system. Moreover, although the mechanism is not well understood, it has been found that the presence of a small amount of the acid appears in many cases to enhance the degree of encapsulation of the insulin by the biocompatible polymer. When used, the acid should typically be at only low concentrations. Typically, the concentration of the acid in the cosolvent system will be smaller than about 10 mM, with a range of from about 1 mM about 3 mM being generally more preferred for most situations.

A further enhancement to the manufacture process when making multi-component particles including the biocompatible polymer is to prepare a first solution including the insulin and at least the first organic solvent and a second solution including the biocompatible polymer and at least the second organic solvent, and to mix the first solution and the second solution during preparation of the feed solution (102). Also, it is further preferred that the second solution be added to the first solution, to prevent precipitation of the insulin, which is often more susceptible to coming out of solution if the first solution is added to the second solution.

When the acid is to be included in the feed solution (102), it is preferred that the first solution include the acid prior to mixing with the second solution. As a further enhancement, it is preferred that the first organic solvent be preacidified by addition of the acid to the first organic solvent prior to dissolution of the insulin to prepare the first solution.

When an acid is used, it is generally desirable to use the lowest acid concentration possible. In one embodiment, the insulin is in the cosolvent system in the form of a colloidal suspension when the feed solution (102) is contacted with the anti-solvent feed (104) (referring again to FIG. 1). The biocompatible polymer, however, will still typically be dissolved in the cosolvent system in the form of a true solution. This will often be the case, for example, when the first organic solvent is a lower alcohol and the acid addition is extremely small, or when an acid is not used at all. It has been found with the present invention that processing the insulin into the form of a colloidal suspension in the cosolvent system produces high quality powders, and permits the use of lower concentrations of the acid or an elimination of the acid altogether in some instances, which is generally preferred. Another example of a cosolvent system where the insulin may be in the form of a colloidal suspension in the cosolvent system is when the first organic solvent is DMSO and the second organic solvent is methylene chloride, especially when the proportion of DMSO is relatively small. The processing of insulin in the form of a colloidal suspension is an important and advantageous aspect of the present invention.

Another possible enhancement with the manufacture process, whether making single-component or multi-component particles, is to maintain the concentration of dissolved insulin in the cosolvent system at a relatively low level. Preferably, the concentration of insulin in the cosolvent system is smaller than about 3 mg (and more preferably in a range of from about 0.3 to about 3 mg) of insulin per milliliter of the cosolvent system. When making single component insulin particles, a preferred range of insulin concentration is from about 0.5 to about 3 mg (more preferably from about 0.5 to about 2 mg) of insulin per milliliter of the cosolvent system. When making multi-component particles, a preferred range of insulin concentration is from about 0.3 to about 1 mg (more preferably from about 0.4 to about 0.8 mg) of insulin per milliliter of the cosolvent system. Operating according to the present invention using a cosolvent system with a relatively low concentration of dissolved insulin has been found to advantageously promote the precipitation of insulin powders suited for use in pulmonary delivery applications. Furthermore, processing is less affected by geometric changes in processing equipment and, accordingly, the process of the present invention lends itself to scale-up. For example, with the process of the present invention, it is typically possible to introduce the feed solution into the compressed anti-solvent without requiring the introduction to be accomplished using a small diameter capillary or orifice. For example, some prior art processes for compressed anti-solvent precipitation of insulin operated at high insulin concentrations in the feed solution and/or introduced the insulin into the compressed anti-solvent fluid through a very small orifice, such as 50 microns or smaller. With the use of the present invention, by processing insulin at a relatively low concentration and using the cosolvent system, the feed solution (102) may be introduced into the anti-solvent fluid through a significantly larger opening while maintaining a high quality powder product. This is important because with large orifices, precipitation would not be expected to proceed as quickly as when using a small orifice, and powder quality could, accordingly, suffer. Therefore, the ability to introduce the feed solution (102) through a larger opening with the present invention while maintaining a high quality product is significant. In one embodiment of the present invention, the feed solution (102) may be introduced into the compressed anti-solvent through an opening having a cross-sectional area available for flow that is larger than about 0.02 square millimeter. In one enhancement, the feed solution (102) is sprayed into the compressed anti-solvent through a spray nozzle having an area available for flow at the outlet of larger than about 1 square millimeter, more preferably larger than about 5 square millimeters and even more preferably larger than about 10 square millimeters.

As another enhancement for the operation of the process of the present invention, also applicable to manufacturers of either single-component or multi-component powders, it has been found that the quality of powders produced may be enhanced by introducing the feed solution (102) into the compressed anti-solvent fluid in a manner to promote more rapid mixing of the feed solution (102) with the compressed anti-solvent fluid, thereby promoting more rapid precipitation from the feed solution (102). In that regard, the feed solution (102) is typically introduced into a significantly larger volume of the flowing anti-solvent feed (104) under the desired conditions of temperature and pressure. For enhanced performance, it is preferred that the feed solution (102) be introduced into the flowing anti-solvent feed (104) so that the feed solution (102), when introduced into the anti-solvent feed (104), has a direction of flow that is in a range of from about 45° to about 180° relative to the direction of flow of the anti-solvent feed (104). More preferred is for the feed solution (102) to have a direction of flow that is in a range of from about 90° to about 180° relative to the direction of flow of the anti-solvent feed (104). Particularly preferred is for the flow of the feed solution (102) to have a direction of flow of about 180° relative to the direction of flow of the anti-solvent feed (104), in which case the feed solution (102) is introduced into the anti-solvent feed (104) in a direction that is directly counter-current to the flow of the anti-solvent feed (104).

As noted previously, the cosolvent system may include one or more additional solvents in addition to the first organic solvent and the second organic solvent. Preferably, however, substantially all of the solvents in the cosolvent system are organic solvents that are highly expandable by and soluble in the compressed anti-solvent feed. The cosolvent system should, however, typically not include any significant quantity of water, because water is highly susceptible to phase separation during processing and its presence tends to significantly impair the quality of the powder that is obtained from the process. Although it may appear that the addition of water could be beneficial to help solubilize the insulin, it has been found that detrimental aspects of using water during processing outweigh any potential benefits. Although it is preferred that the cosolvent system be substantially free of water, when water is present it should comprise less than about 5 weight percent of the cosolvent system.

In a further aspect, a significant advantage of using the process of the present invention is that it is not necessary to ion pair the insulin with amphiphillic materials in order to solubilize the insulin for processing to make a high quality powder. Rather, using the cosolvent system with the process of the present invention, no such ion pairing is required to make a high quality insulin product. Furthermore, when an insulin-containing powder is prepared according to the process of the present invention, it is possible to manufacture a powder of a free flowing nature with good particle characteristics for aerosolization for pulmonary delivery applications and without significant degradation of the insulin being observed.

In another aspect, the present invention provides insulin-containing powders, particularly suited for use in pulmonary delivery applications, manufacturable by the manufacture method of the present invention as just described. Advantageously, the powders of the present invention are frequently free flowing and highly dispersable. By free flowing, it is meant that the particles of the powder do not tend to strongly adhere to each other or to the surfaces of storage or processing equipment. The result is that the powders are frequently advantageously amenable to processing and handling encountered during measurement and packaging operations without excessive difficulty or excessive powder losses. By highly dispersable, it is meant that the particles tend to be easy to disperse, or separate from each other. A high degree of dispersability is desirable to permit the powder to be easily aerosolized to prepare an aerosol that does not contain a large quantity of excessively large aggregate units. Furthermore, the powders of the present invention typically are aerosolizable to produce an aerosol having dispersed insulin-containing particles advantageously having aerodynamic diameters in a range of from about 1 micron to about 6 microns. Advantageously, the dispersed insulin-containing particles in the aerosol typically will have a mass median aerodynamic diameter of smaller than about 6 microns, and more preferably the mass median aerodynamic diameter will be in a range having a lower limit of about 1 micron and an upper limit of about 6 microns, more preferably about 5 microns, and even more preferably about 4 microns. Particularly preferred is for the dispersed insulin-containing particles in the aerosol to have a mass median aerodynamic diameter in a range of from about 1 micron to about 3 microns. As will be appreciated, these stated size characteristics for particles in an aerosol are in reference to the insulin-containing particles of the present invention that are present in the aerosol. It is also possible that the aerosol may contain other particles, and that these other particles may be of a larger or smaller size. For example, the aerosol may include larger particles of a bulking agent, such as of lactose or another material now or hereafter known to be used for bulking purposes. This would be the case when an insulin-containing powder made by the manufacture method of the present invention is mixed with a bulking agent to form a powder mixture with modified handling characteristics or to cut the concentration of insulin in the powder mixture. Such mixed powders are within the scope of the invention, and in such situations, the properties described herein for the insulin-containing powders of the present invention refer to the properties of only that portion of such a powder mixture composed of the insulin-containing particles of the present invention.

Furthermore, the insulin-containing powder of the present invention, as recovered from the manufacture process, is often in the form of relatively large aggregates of primary particles. This is often the case, for example, with the multi-component particles including insulin and a biocompatible polymer. These aggregate units may include 100 or more primary particles and typically have a mass average envelope diameter of larger than about 25 microns, and frequently larger than about 50 microns, with the mass average envelope diameter typically being determinable from analysis of micrographs of a representative powder sample, which analysis may be performed manually or with the use of software analysis techniques. The primary particles, however, typically have a mass median diameter of smaller than about 6 microns, more often smaller than about 5 microns and preferably smaller than about 4 microns. These aggregates, however, can typically be broken up, either prior to or during aerosolization to permit production of an aerosol having the desired characteristics, as previously discussed.

In one embodiment, the insulin-containing powder of the present invention is made using a co-solvent system for manufacture, as previously described. One problem historically encountered with the manufacture of insulin-containing powders is that it has been difficult to produce powders with desirable properties for use in pulmonary delivery applications. It has surprisingly been found, however, that with the present invention, insulin-containing powders are manufacturable that frequently include advantageous properties for pulmonary delivery applications, using the co-solvent processing technique previously described. The powders may include the insulin in single component particles of substantially pure insulin, or may include multi-component particles, such as those including a biocompatible polymer to promote sustained release of the insulin, as previously described. Moreover, although the powders of the present invention have been identified as being particularly well suited for use in pulmonary delivery applications, it should be recognized that use of the powders is not so limited. Rather, the powders may be used in any application in which an insulin-containing powder is desired, including for example intranasal, injection, oral and dermal applications.

In one embodiment, the insulin-containing powder of the present invention includes multi-component particles having at least insulin and a biocompatible polymer, and having a high degree of insulin encapsulation, so that the powder is advantageously suited for sustained release of the insulin when administered to a subject. The degree of insulin encapsulation of the powder provides an indication as to the degree to which insulin will be released from the powder over time relative to a substantially pure insulin powder. As used herein, the degree of insulin encapsulation of a powder is determined by the following procedure: A 60 milligram sample of the powder in a substantially dry form is immersed in 30 milliliters of a phosphate buffer solution (PBS) containing a small amount of a dispersing agent and maintained at a temperature of approximately 37° C., and the quantity of insulin remaining in the powder 15 minutes after immersion is determined. Any suitable PBS solution may be used. A preferred PBS includes 137 mM NaCl, 10.2 mM $NaHPO_4.7H_2O$ (dibasic sodium phosphate septahydrate), 1.8 mM $KH_2PO_4$ (monobasic potassium phosphate), 2.7 mM KCl and 3.1 mM $NaN_3$ (sodium azide). A small amount of dispersing agent (nonionic surfactant preferred) should be included in the PBS to help keep the powder in a dispersed state during the test. A preferred dispersing agent is Tween™ 20 (polyethylene 20 sorbitan surfactant), or an equivalent nonionic surfactant, which is preferably added in an amount of about 0.2 grams per liter of the PBS, or such other quantity as is required to substantially disperse the particles in the PBS. The Tween™ family of surfactants is well known and such surfactants are available, for example, from Fisher Scientific International, Inc. The degree of insulin encapsulation is equal to the percentage of insulin remaining in the powder after 15 minutes relative to the quantity of insulin originally contained within the powder prior to immersion in the PBS. The PBS may be provided in any convenient container, such in as a 50 milliliter polypropylene centrifuge tube. The powder is immersed in the PBS by adding the insulin to the PBS accompanied by thorough mixing to disperse the powder in the PBS. The mixing may be accomplished by vortexing or shaking. The quantity of insulin remaining in the insulin is determined by first determining the quantity of insulin that has dissolved in the PBS during the test and then determining the quantity of insulin remaining in the powder by difference. The quantity of insulin that has been dissolved in the PBS is determined by taking a sample of the PBS 15 minutes after immersion and measuring the concentration of insulin dissolved in the PBS, by a suitable technique, such as by HPLC (high-performance liquid chromatography). A degree of insulin encapsulation of 0% indicates that substantially all of the insulin dissolves in the PBS during the test and an insulin encapsulation of 100% indicates that substantially none of the insulin dissolves in the PBS during the test.

Manufacture of the multi-component powder of the present invention with a high degree of insulin encapsulation is particularly noteworthy. It has been found with the present invention that manufacture using the cosolvent system processing technique previously described is conducive to manufacture of the multi-component particles with a high degree of insulin encapsulation. Furthermore, even when using the cosolvent system, the degree of encapsulation is often enhanced by operation of the manufacture process under controlled conditions, such as by acidification of the co-solvent system and/or preferred orientation of the flow of the feed solution to the flow of the anti-solvent, as previously discussed. Furthermore, by varying manufacture conditions, it is possible to vary the degree of encapsulation. For example, The degree of insulin encapsulation desired in the multi-component powder will depend upon the insulin release characteristics desired for the particular application of interest. For some applications it may be desirable that at least some of the insulin immediately release for immediate therapeutic effect, and that the remaining insulin be released over a longer period to prolong the therapeutic effect. In most instances, however, the multi-component powder will typically have a degree of insulin encapsulation of larger than about 30%, preferably larger than about 50%, more preferably larger than about 60%, still more preferably larger than about 70%, and most preferably larger than about 80%. In some instances, the degree of insulin encapsulation may be larger than about 90%.

The biocompatible polymer may be any suitable biocompatible polymer. Exemplary biocompatible polymers are as previously described in the discussion concerning the manufacture method. Furthermore, the multi-component particles may include the biocompatible polymer and the insulin in any desired proportions, such as those previously described in the discussion concerning the manufacture method.

In another aspect, the present invention provides a packaged insulin-containing powder product, with at least one powder batch contained within a receptacle, that is either a part of or adapted to be operable with an inhaler, most typically a dry powder inhaler capable of generating an insulin-containing aerosol for pulmonary delivery of insulin to a subject when inhaled by the subject. The product includes an insulin-containing powder of the present invention, as described previously, contained within the receptacle, in a manner so that at least a portion of the insulin-containing powder is removed from the receptacle and aerosolized by the inhaler when the inhaler is actuated. The insulin-containing powder contained in the receptacle may be any insulin-containing powder of the present invention, such as, for example, substantially pure insulin powder or multi-component powder including insulin and a biocompatible polymer. In a preferred embodiment, however, the insulin-containing powder is a multi-component powder including a degree of insulin encapsulation of at least about 50%.

The receptacle may be any suitable receptacle that is adapted to be received by and to operatively cooperate with an inhaler, so that the inhaler is capable of being actuated to remove at least a portion of the insulin-containing powder from the receptacle to generate an aerosol including insulin-containing particles dispersed in a carrier gas, for inhalation by a subject for pulmonary delivery of insulin. Therefore, the receptacle for any particular embodiment will typically be designed for use with a particular dry powder inhaler. Several different inhaler/receptacle designs are known in the art, and any such receptacle may be used with this aspect of the present invention. Furthermore, the present invention includes receptacle designs that will inevitably be designed in the future to cooperate with new inhaler designs.

In one embodiment, the receptacle contains at least one compartment including a unit dose of insulin, meaning that actuation of the inhaler to produce an aerosol from the insulin-containing powder contained in the compartment will result in production of an aerosol containing a quantity of insulin sufficient to provide substantially only a single therapeutically effective dose of insulin to a subject when the aerosol is inhaled by the subject. In a preferred embodiment, the receptacle is a multi-compartment receptacle and includes a plurality of such compartments, with each compartment including a unit dose of insulin, so that when the receptacle is operably received by an inhaler, the inhaler is capable of being sequentially actuated, with each actuation aerosolizing insulin-containing powder from a different one of the compartments to provide an aerosol with a single dose of insulin for inhalation by a subject. For example, one type of multi-component receptacle is a multi-compartment blister pack adapted to be received by and to operably cooperate with a dry powder inhaler. Such a multi-component blister pack could be made in any convenient geometric form as dictated for use with any particular inhaler design, such as, for example, in the form of a blister ring, a blister disk, or a blister strip. Another type of multi-component receptacle is a multi-compartment cartridge. Such cartridges may be made in any convenient geometric form as dictated for use with any particular inhaler design, such as, for example, in the form of a cartridge ring, cartridge disk or cartridge strip. As will be appreciated, the compartment(s) of the receptacle may be sealed to protect the insulin prior to use, or may be unsealed, but enclosed within the inhaler in a manner to adequately protect the insulin. In one embodiment, the receptacle acts to transfer measured quantities of insulin-containing powder for a bulk reservoir of powder contained within the inhaler for use to produce unit dose aerosols when the inhaler is actuated. In a preferred embodiment, however, the compartment(s) of the receptacle will each initially be filled with a unit dose of insulin and will each be sealed substantially until aerosolization of the unit dose when the inhaler is actuated.

As will be appreciated, any number of designs and particular structures are possible for such a multi-compartment receptacle. Nonlimiting examples of suitable multi-component receptacles, and corresponding dry powder inhalers, useful with the present invention are disclosed in U.S. Pat. No. 5,503,869 (various medicament carrier cassette designs); International Patent Publication No. WO 98/04308 (various medicament carrier cassette designs);

European Patent Publication EP 0 069 715 (perforated membrane); U.S. Pat. No. 5,460,173 (screened disc structure), U.S. Pat. No. 5,619,984 (flexible carriers), U.S. Pat. No. 5,794,613 (disc-shaped disperser with multiple cavities); and U.S. Pat. No. 5,875,776 (dosing carousel).

In another aspect, the present invention provides an apparatus for pulmonary delivery of insulin. An insulin-containing powder of the present invention, as described previously, is disposed within an inhaler that is actuatable to aerosolize at least a portion of the powder to produce an aerosol including substantially a single dose of a therapeutically effective amount of insulin inhalable by a subject. The insulin-containing powder is preferably contained within a receptacle, as previously described, operably engaged with or being an integral part of the inhaler. In a preferred embodiment, the receptacle is a multi-component receptacle, as previously described, with each component including a unit dose powder batch, and the inhaler is successively actuatable, so that each successive actuation aerosolized at least a portion of a powder batch in a different one of the compartments. In another embodiment, however, the inhaler may be a single dose inhaler, meaning that the receptacle is a single compartment receptacle including only a single unit dose of insulin. This would be the case, for example, when the inhaler is a single use inhaler, which could be designed to be disposable or refillable after the single use. The inhaler may be any desired inhaler design. In a preferred embodiment, the inhaler will be a dry powder inhaler. In another embodiment, the inhaler will be a metered dose inhaler, in which the insulin-containing powder is suspended in a propellant fluid that is in a liquid state prior to actuation and which expands and substantially vaporizes when the inhaler is actuated to produce an aerosol. The propellant fluid may be a halocarbon, such as fluorochlorocarbons currently being phased out, or new classes of propellant fluids being identified to replace fluorochlorocarbons.

EXAMPLES

The examples presented below are representative of certain aspects of the present invention and are not intended to demonstrate every aspect of the present invention. These examples are provided to further aid understanding of the present invention, and are not limiting of the scope of the present invention.

The materials used in the examples are as follows:

DMSO: Reagent grade from Sigma-Aldrich Corp. (Aldrich)
HCl: Reagent grade from Fisher Scientific International Inc. (Fisher)
Methanol (MeOH): HPLC grade from Fisher
Isopropyl alcohol (i-PrOH): HPLC grade from Fisher
Methyline chloride (MeCl$_2$): HPLC grade from Fisher
Acetonitrile: HPLC grade from Fisher
Carbon dioxide: USP grade from General Air, Inc.
Bovine insulin: Pancreas derived bovine insulin (zinc salt form) from Aldrich
Human insulin: Recombinant human insulin (zinc salt form) from Aldrich
Poly(1-lactic acid) (L-PLA): Medical grade from Boehringer Ingelheim
Dibasic sodium phosphate septahydrate: Reagent grade from Fisher
Sodium chloride: Reagent grade from Fisher
Potassium chloride: Reagent grade from Fisher
Tween 20™: Enzyme grade from Fisher
Monobasic potassium phosphate: Reagent grade from Fisher
Sodium azide: Reagent grade from Aldrich Example 1

This example demonstrates manufacture of single-component powders including substantially only insulin according to the manufacture method of the present invention using a feed solution including a cosolvent system.

Feed solutions are prepared including insulin dissolved in a variety of cosolvent systems at a concentration of about 1–2 mg/mL. The feed solution is contacted in countercurrent flow with supercritical compressed carbon dioxide as an anti-solvent flowing through a precipitation chamber at a temperature of about 37±2° C. and a pressure of about 83.6±1.4 atm to precipitate insulin from the feed solution. The precipitation chamber is a stainless steel chamber about 20 cm long and having a square cross-section of about 2 cm by 2 cm. The compressed carbon dioxide is delivered to the chamber via a pressure regulator and is introduced into the top of the chamber. The feed solution is delivered to the chamber via a syringe pump and is introduced into the flowing carbon dioxide anti-solvent in countercurrent flow though a 160 micron diameter stainless steel capillary tube located in the upper part of the chamber approximately in the middle of the stream of flowing carbon dioxide anti-solvent. The flow rate of the carbon dioxide is maintained at about 50±1 mL/min and the flow rate of the feed solution is maintained at about 1±0.1 mL/min. The precipitated particles are collected on either a polyvinylidene fluoride (PVDF) filter or a polytetrafluoroethelyne (PGLP) filter (0.2 micron) located outside of the chamber.

As shown in Table 1, tests 1–4 are comparative tests using DMSO, DMFA or methanol as the only solvent in the feed solution, with tests 2–4 including addition of a small quantity of HCl (2.4 mM in feed solution). Tests 5–11 demonstrate processing using a cosolvent system with DMSO as the first organic solvent and methanol, isopropyl alcohol, methylene chloride, (iPrOH), methylene chloride (CH$_2$Cl$_2$) or acetonitrile—as the second organic solvent, with various weight ratios of the first organic solvent to the second organic solvent being used ranging from 10:90 to 50:50, as shown in Table 1. Bovine insulin is used in some tests and human insulin in other tests.

For the comparative tests (Tests 1–4), the feed solutions are each prepared by dissolving the insulin in the organic solvent at room temperature with stirring, with the first organic solvent being preacidified with the HCl when used. For the tests involving use of a cosolvent system, the feed solutions are each prepared by first dissolving the insulin in the first organic solvent (DMSO) at room temperature with stirring. To this solution is then slowly added the second organic solvent with stirring and the resulting mixture is stirred for an additional 10 minutes prior to loading into the syringe pump.

Results of the tests are shown in Table 1. As seen in Table 1, the powders prepared in the comparative tests are non-free flowing and are not desirable for use in pulmonary delivery applications. The powders prepared using the cosolvent system (tests 5–12) are free-flowing powders and more desirable for use in pulmonary delivery applications. Test 13 shows the detrimental impact on powder quality of including 5% water in a cosolvent system including DMSO and methanol.

Moreover, it is noted that during the preparation of the feed solutions for tests 6 through 12, insulin precipitated to form a colloidal suspension in the feed solution when the isopropyl alcohol was added to the DMSO/insulin solution.

These tests also result in preparation of free flowing powders.

TABLE 1

| Test | Solvent System | Insulin Source | Powder Characteristics |
|---|---|---|---|
| 1 | DMSO | Bovine | Granular non-free flowing powder |
| 2 | DMSO, HCl (2.4 mM) | Bovine/Human | Granular non-free flowing powder |
| 3 | DMF, HCl (2.4 mM) | Bovine | Granular non-free flowing powder |
| 4 | MeOH, HCl (2.4 mM) | Bovine | Fluffy non-free flowing powder |
| 5 | DMSO, MeOH (50:50) | Human | Fluffy free flowing powder |
| 6 | DMSO, iPrOH (50:50) | Human | Fine free flowing powder |
| 7 | DMSO, iPrOH (40:60) | Human | Fine free flowing powder |
| 8 | DMSO, iPrOH (20:80) | Human | Fine free flowing powder |
| 9 | DMSO, iPrOH (10:90) | Human | Fine free flowing powder |
| 10 | DMSO, $CH_2Cl_2$ (50:50) | Human | Fluffy free flowing powder |
| 11 | DMSO, Acetonitrile (50:50) | Human | Fluffy free flowing powder |
| 12 | DMSO, MeOH (20:80) | Human | Fluffy free flowing powder |
| 13 | DMSO, MeOH, $H_2O$ (20:75:5) | Human | Gummy material |

Example 2

This example demonstrates the manufacture of multi-component particles including insulin and a biocompatible polymer according to the manufacture method of the present invention using a feed solution including a cosolvent system.

Feed solutions are prepared including various molecular weight poly(L-lactic acid) and human insulin in different solvent systems. Tests 14 and 15 are comparative tests using a single solvent (DMSO), while tests 16–37 use various cosolvent systems with either DMSO or methanol as the first organic solvent and methylene chloride as the second organic solvent. Insulin loading is varied from 7% to 50% by weight (based on weight of insulin relative to total weight of insulin medium plus polymer). Each feed solution is prepared in 50 mL batches generally by the following procedure: DMSO or methanol is acidified with concentrated HCl to provide the desired level of acidification and the insulin is then dissolved into the resulting acidified solvent with stirring at room temperature. For comparative tests 14 and 15, the desired amount of the polymer is then dissolved in the insulin/DMSO solution with stirring at room temperature. For the other tests, the polymer is instead dissolved in methylene chloride in a separate container to form a second solution with stirring at room temperature. The polymer/methylene chloride solution is then slowly added to the insulin/DMSO or the insulin/methanol solution, as the case may be, with stirring at room temperature, with the resulting mixture being stirred an additional 2–5 minutes prior to being loaded into the syringe pump. The quantities of ingredients per 50 mL batch for each test is shown in Table 2.

The feed solutions are contacted with compressed carbon dioxide anti-solvent under conditions similar to those described for Example 1. For each powder, the degree of insulin encapsulation is determined by in vitro testing involving immersing a 6 mg sample of the powder in 30 mL of PBS (prepared as previously described to include 137 mM NaCl, 10.2 mM $NaHPO_4.7H_2O$, 1.8 mM $KH_2PO_4$, 2.7 mM KCl and 3.1 mM $NaN_3$) and determining the percentage of insulin dissolution into the PBS according to the procedure previously described by monitoring insulin concentration in the PBS by HPLC analysis. Tests 14 and 15 are comparative tests demonstrating use of a single-solvent system (DMSO).

Figure 3:
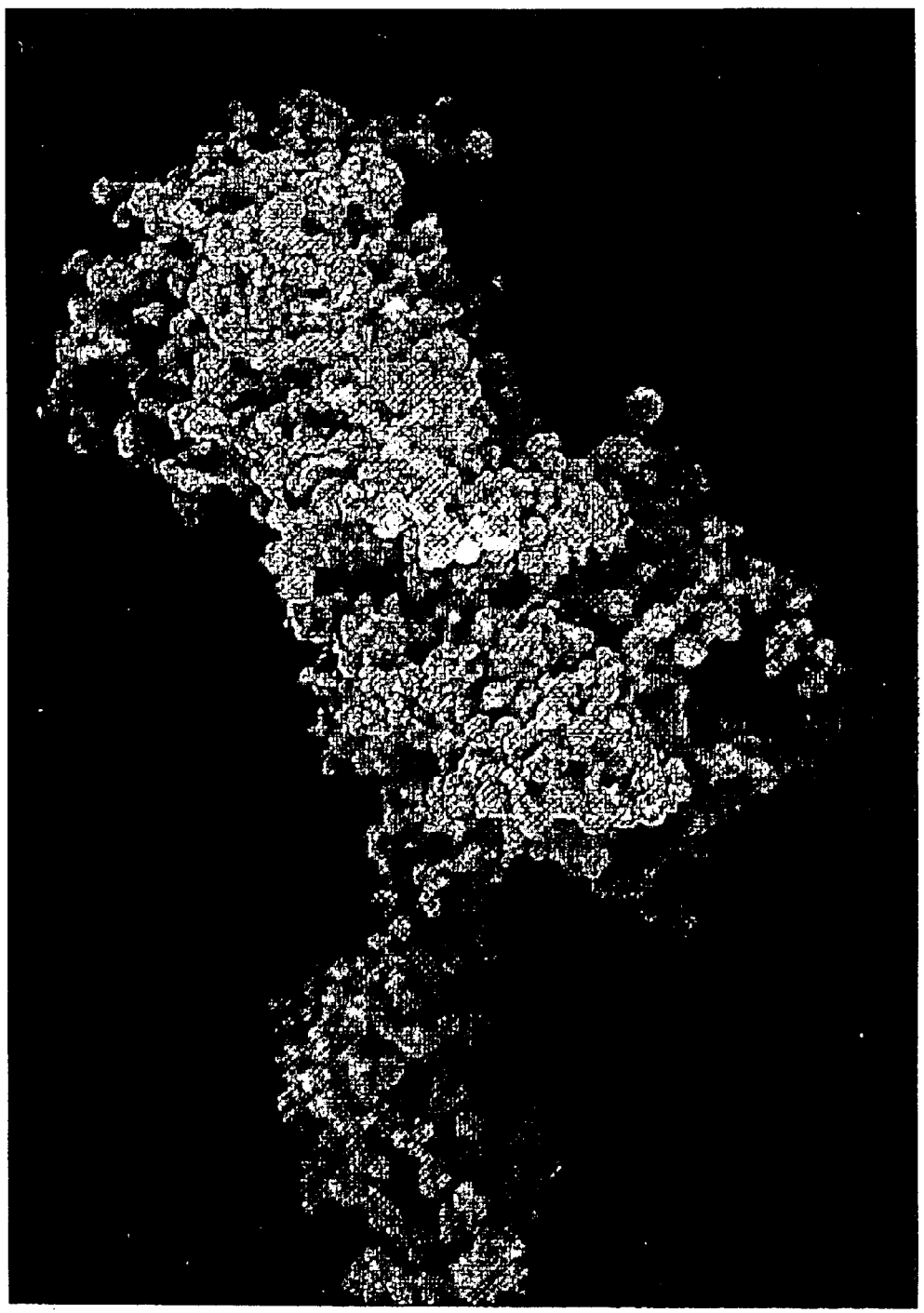
FIG. 3 is a photomicrograph showing an aggregate structure from an insulin-containing powder of the present invention.

A summary of the solvent systems and results of the tests are shown in Table 3. As shown in Table 3, substantial encapsulation of the insulin is more difficult to obtain when using low molecular polymers. It is also seen, however, that the use of a cosolvent system generally results in significantly higher insulin encapsulation than the single solvent, especially for tests using higher molecular weight polymer. Also, the tests using methanol and methylene chloride in the cosolvent system generally show a higher degree of insulin encapsulation than the tests using DMSO and methylene chloride in the cosolvent system. Furthermore tests 21, 25, and 35–37 show preparation of powders having over 50% insulin encapsulation even when the powders include high levels of insulin loading. Table 3 also shows the level of burst demonstrated by each of the powders during the in vitro testing. The burst is the percentage of the polymer that is released during the first 15 minutes after immersion in of the sample the PBS. FIG. 3 shows a photomicrograph of a representative sample from test 33 showing an aggregate of the particulate product comprised of micron to submicron primary particles. The main body of the aggregate structure has a width of about 10 microns and a length of about 40 microns.

TABLE 2

| Test | DMSO (mL) | MeOH (mL) | Conc. HCl (uL) | $CH_2Cl_2$ (mL) | Insulin (mg) | Polymer (mg) | Polymer MW (kDa) |
|---|---|---|---|---|---|---|---|
| 14 | 250 | 0 | 25 | 0 | 504 | 500 | 2 |
| 15 | 116 | 0 | 30 | 0 | 405 | 408 | 26 |
| 16 | 98 | 0 | 10 | 2 | 201 | 201 | 26 |
| 17 | 98 | 0 | 10 | 6 | 201 | 611 | 100 |
| 18 | 90 | 0 | 10 | 10 | 200 | 201 | 26 |
| 19 | 50 | 0 | 10 | 50 | 203 | 207 | 2 |
| 20 | 50 | 0 | 10 | 50 | 208 | 203 | 26 |
| 21 | 50 | 0 | 10 | 50 | 202 | 201 | 100 |
| 22 | 25 | 0 | 10 | 75 | 201 | 203 | 2 |
| 23 | 25 | 0 | 10 | 75 | 101 | 1001 | 2 |
| 24 | 25 | 0 | 10 | 75 | 100 | 994 | 100 |
| 25 | 0 | 10 | 10 | 90 | 61 | 204 | 100 |
| 26 | 0 | 40 | 10 | 60 | 60 | 742 | 100 |
| 27 | 0 | 15 | 10 | 85 | 60 | 749 | 100 |
| 28 | 0 | 15 | 10 | 85 | 60 | 202 | 100 |
| 29 | 0 | 70 | 20 | 186 | 141 | 1878 | 100 |
| 30 | 0 | 27 | 10 | 73 | 56 | 728 | 100 |
| 31 | 0 | 14 | 10 | 37 | 27 | 365 | 100 |
| 32 | 0 | 28 | 10 | 74 | 62 | 446 | 100 |
| 33 | 0 | 28 | 20 | 74 | 61 | 459 | 100 |
| 34 | 0 | 14 | 20 | 37 | 51 | 354 | 100 |
| 35 | 0 | 56 | 40 | 148 | 126 | 376 | 100 |
| 36 | 0 | 40 | 20 | 60 | 201 | 203 | 100 |
| 37 | 0 | 14 | 20 | 37 | 195 | 191 | 100 |

TABLE 3

| Test | Solvent System | | | | Insulin Load (%) | Insulin Burst (%) | Insulin Encapsulation (%) |
| --- | --- | --- | --- | --- | --- | --- | --- |
| | DMSO (%) | MeOH (%) | $CH_2Cl_2$ (%) | HCl (mM) | | | |
| 14 | 100 | 0 | 0 | 1.2 | 50 | 100 | 0 |
| 15 | 100 | 0 | 0 | 1.8 | 50 | 72 | 28 |
| 16 | 98 | 0 | 2 | 1.2 | 50 | 73 | 27 |
| 17 | 94 | 0 | 6 | 1.2 | 25 | 85 | 15 |
| 18 | 90 | 0 | 10 | 1.2 | 50 | 86 | 14 |
| 19 | 50 | 0 | 50 | 1.2 | 50 | 100 | 0 |
| 20 | 50 | 0 | 50 | 1.2 | 51 | 76 | 24 |
| 21 | 50 | 0 | 50 | 1.2 | 50 | 49 | 51 |
| 22 | 25 | 0 | 75 | 1.2 | 50 | 100 | 0 |
| 23 | 25 | 0 | 75 | 1.2 | 9 | 66 | 34 |
| 24 | 25 | 0 | 75 | 1.2 | 9 | 51 | 49 |
| 25 | 0 | 10 | 90 | 1.2 | 23 | 11 | 89 |
| 26 | 0 | 40 | 60 | 1.2 | 8 | 43 | 57 |
| 27 | 0 | 15 | 85 | 1.2 | 7 | 20 | 80 |
| 28 | 0 | 15 | 85 | 1.2 | 23 | 56 | 44 |
| 29 | 0 | 27 | 73 | 0.9 | 7 | 50 | 50 |
| 30 | 0 | 27 | 73 | 1.2 | 7 | 37 | 63 |
| 31 | 0 | 27 | 73 | 2.4 | 7 | 15 | 85 |
| 32 | 0 | 27 | 73 | 1.2 | 12 | 24 | 76 |
| 33 | 0 | 27 | 73 | 2.4 | 12 | 1 | 99 |
| 34 | 0 | 27 | 73 | 4.8 | 13 | 26 | 74 |
| 35 | 0 | 27 | 73 | 2.4 | 25 | 7 | 93 |
| 36 | 0 | 40 | 60 | 2.4 | 50 | 40 | 60 |
| 37 | 0 | 27 | 73 | 4.8 | 50 | 34 | 66 |

Example 3

This example demonstrates sustained release of insulin in animal studies by pulmonary delivery using multi-component particles including insulin and a biocompatible polymer.

A powder of substantially pure insulin, of the type as prepared in Test 2 shown in Example 1, and a powder of multi-component particles, of the type as prepared in Test 33 of Example 2 (including 12% by weight insulin and 88% by weight of 100 k Da L-PLA), are administered intratracheally to male rabbits. Blood samples are taken prior to administration and periodically over a 24 hour period following administration and analyzed for insulin concentration.

Male rabbits weighing about 3 Kg are treated and/or anesthetized with atropine (subcutaneous), acepromazine (intramuscular) and halothane (inhalation). Intratracheal drug placement is accomplished using a pediatric bronchoscope. An aqueous suspension of the powder (11.16 mg powder/mL of water) is administered with a syringe and catheter placed inside an endotracheal tube. Each rabbit receives 12.5 units of insulin per Kg of animal weight. Periodically, 1.5 mL blood samples are collected from blood vessels in the ear and placed in EDTA tubes. Plasma is separated from each blood sample and tested for insulin concentration by radio immunoassay.

Figure 2:
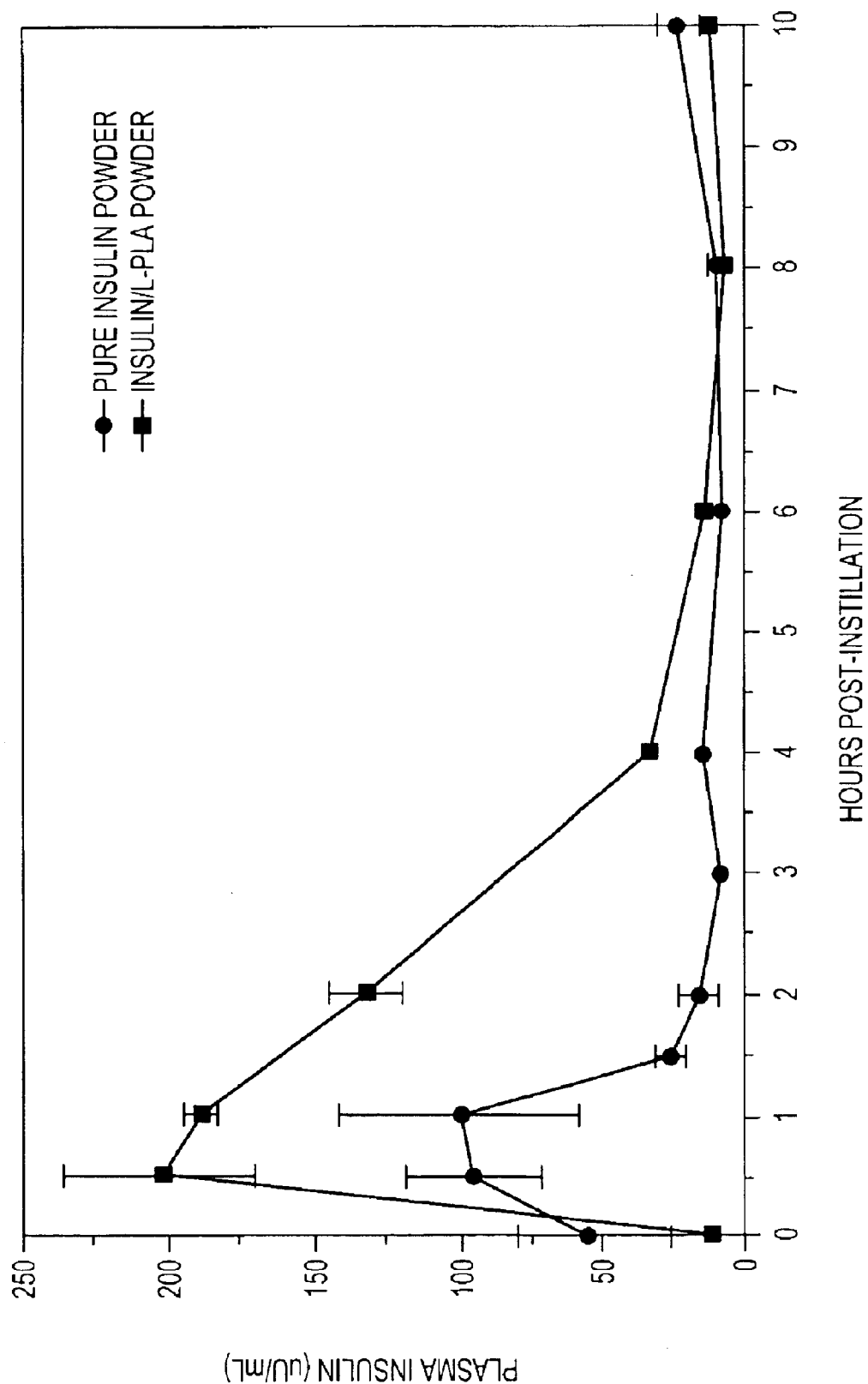
FIG. 2 is a plot showing blood plasma insulin concentration vs time following administration of multi-component particles of the present invention to a rabbit as described in Example 3.

FIG. 2 shows a plot of measured insulin concentration in the plasma in microunits of insulin per mL of plasma for each of the pure insulin powder and the encapsulated insulin powder over a period of 8 hours following intratracheal placement. As seen in FIG. 2, use of the encapsulated insulin powder results in the presence of a significantly elevated insulin concentration in the plasma for an extended time relative to the pure insulin powder.

While various embodiments of the present invention have been described in detail, it should be understood that any feature of any embodiment may be combined with any other feature of any other embodiment. For example, any compatible combination of cosolvent system, biocompatible polymer and insulin loading may be processed according to the method of manufacture. Furthermore, any of the insulin-containing particulate products may be incorporated into an inhaler or a receptacle adapted for use with an inhaler. Such compatible combinations are expressly included within the scope of the present invention. Moreover, while various embodiments of the present invention have been described in detail, it is apparent that modifications and adaptations of those embodiments will occur to those skilled in the art. It is to be expressly understood, however, that such modifications and adaptations are within the scope of the present invention, and it is intended that the appended claims be interpreted to the broadest coverage extent possible in light of applicable prior art.

What is claimed is:

1. A method for making a particulate product containing insulin, the method comprising:
    contacting a feed solution containing insulin with a compressed anti-solvent fluid to precipitate particles containing insulin, the feed solution including the insulin in a cosolvent system, the cosolvent system comprising a first organic solvent and a second organic solvent that are mutually soluble, the first organic solvent and the second organic solvent not being the same; and
    separating the particles from the first organic solvent, the second organic solvent and the anti-solvent fluid;
    wherein the contacting comprises extracting the first organic solvent and the second organic solvent into the anti-solvent fluid; and
    wherein the first organic solvent and the second organic solvent are present in the cosolvent system at a volume ratio of the second organic solvent to the first or organic solvent of from 10:90 to 99:1.

2. The method of claim 1, wherein insulin is at least 10 times more soluble in the first organic solvent than in the second organic solvent.

3. The method of claim 1, wherein the first organic solvent and the second organic solvent are present in the cosolvent system at a volume ratio of the second organic solvent to the first organic solvent of larger than 30:70.

4. The method of claim 1, wherein the first organic solvent and the second organic solvent are present in the cosolvent system at a volume ratio of the second organic solvent to the first organic solvent of from 50:50 to 90:10.

5. The method of claim 1, wherein the first organic solvent is selected from the group consisting of dimethyl sulfoxide and dimethyl formamide.

6. The method of claim 5, wherein the second organic solvent is an alcohol.

7. The method of claim 5, wherein the second organic solvent is a C1–C5 alkanol.

8. The method of claim 1, wherein the first organic solvent and the second organic solvent are present in the cosolvent system at a volume ratio of the second organic solvent to the first organic solvent of from 10:90 to 90:10.

9. The method of claim 8, wherein the concentration of insulin in the cosolvent system is smaller than 3 mg of insulin per milliliter of the feed solution.

10. The method of claim 8, wherein the concentration of insulin in the cosolvent system is in a range of from 0.3 to 3 mg of insulin per milliliter of the solution.

11. The method of claim 9, wherein the compressed anti-solvent fluid, during the contacting, is at a reduced pressure of larger than 0.9 and a reduced temperature of larger than 0.95, the reduced pressure being a ratio of pressure expressed in atmospheres of the compressed anti-solvent fluid during the contacting to the critical pressure expressed in atmospheres of the compressed anti-solvent fluid, and the reduced temperature being a ratio of temperature expressed in K of the compressed anti-solvent fluid during the contacting to the critical temperature expressed in K of the compressed anti-solvent fluid.

12. The method of claim 11, wherein the compressed anti-solvent fluid, during the contacting step, is in a supercritical state.

13. The method of claim 11, wherein, in the feed solution, the insulin is dissolved in the cosolvent system.

14. The method of claim 13, wherein the feed solution includes a biocompatible polymer and the particles are multi-component particles including the insulin and the biocompatible polymer.

15. The method of claim 14, wherein, in the feed solution, both the insulin and the biocompatible polymer are dissolved in the cosolvent system.

16. The method of claim 1, wherein the compressed anti-solvent fluid, during the contacting, is at a reduced pressure of larger than 0.8 and a reduced temperature of larger than 0.95, the reduced pressure being a ratio of pressure expressed in atmospheres of the compressed anti-solvent fluid during the contacting to the critical pressure expressed in atmospheres of the compressed anti-solvent fluid, and the reduced temperature being a ratio of temperature expressed in K of the compressed anti-solvent fluid during the contacting to the critical temperature expressed in K of the compressed anti-solvent fluid.

17. The method of claim 16, wherein the compressed anti-solvent fluid, during the contacting, is at a reduced pressure of larger than 0.9.

18. The method of claim 16, wherein the compressed anti-solvent fluid, during the contacting, is in a supercritical state.

19. The method of claim 16, wherein the compressed anti-solvent fluid comprises compressed carbon dioxide.

20. The method of claim 1, wherein, during the contacting step, the solution is introduced into the compressed anti-solvent fluid through an opening having a cross-sectional area available for flow that is larger than 1 square millimeter.

21. The method of claim 20, wherein the solution, when introduced into the compressed anti-solvent fluid has a direction of flow that is at an angle of from 45° to 180° relative to the direction of flow of the compressed anti-solvent fluid.

22. The method of claim 1, wherein the cosolvent system comprises up to 5 weight percent water.

23. The method of claim 1, wherein the cosolvent system is free of water.

24. The method of claim 1, wherein the feed solution comprises colloidal particles of the insulin dispersed in the cosolvent system.

25. The method of claim 1, wherein the feed solution includes a biocompatible polymer and the particles are multi-component particles including the insulin and the biocompatible polymer.

26. The method of claim 25, wherein the insulin is more soluble in the first organic solvent than is the biocompatible polymer, and the biocompatible polymer is more soluble in the second organic solvent than the insulin.

27. The method of claim 25, wherein the biocompatible polymer is hydrophobic, the first organic solvent being a polar solvent for the insulin and the second organic solvent being a nonpolar solvent for the biocompatible polymer.

28. The method of claim 25, wherein the first organic solvent is miscible with water and the second organic solvent is immiscible with water.

29. The method of claim 25, wherein the second organic solvent is selected from the group consisting of methylene chloride, formaldehyde, dioxolane, chloroform, benzene, ethyl ether, toluene, xylene, 1,3-dioxane and tetrahydrofuran.

30. The method of claim 24, wherein the first organic solvent comprises an alcohol.

31. The method of claim 30, wherein the first organic solvent comprises a C1–C5-alkanol.

32. The method of claim 31, wherein the first organic solvent is selected from the group consisting of methanol, ethanol and isopropanol.

33. The method of claim 31, wherein the feed solution further comprises an acid dissolved in the cosolvent system.

34. The method of claim 33, wherein the acid comprises an inorganic acid.

35. The method of claim 33 wherein the acid comprises hydrochloric acid.

36. The method of claim 35, wherein the method comprises, prior to the contacting step, preparing the feed solution, comprising mixing a first solution having the insulin dissolved therein with a second solution having the biocompatible polymer dissolved therein, the first solution including the first organic solvent and the second solution including the second organic solvent.

37. The method of claim 36, wherein during the mixing step, the second solution is added to the first solution.

38. The method of claim 36, wherein the first solution comprises an acid to increase the solubility of the insulin in the first solution.

39. The method of claim 35, wherein the second solution is prepared by dissolving the acid in the second organic solvent and then dissolving the insulin in the second organic solvent.

40. The method of claim 25, wherein the weight ratio of the insulin to the polymer in the feed solution is larger than 5:95.

41. The method of claim 25, wherein the weight ratio of the insulin to the polymer in the feed solution is in a range of from 5:95 to 50:50.

42. The method of claim 25, wherein both of the first organic solvent and the second organic solvent are soluble in the compressed anti-solvent fluid, and during the contacting both of the first organic solvent and the second organic solvent are extracted into the compressed anti-solvent fluid.

43. The method of claim 25, wherein the compressed anti-solvent fluid, during the contacting step, is at a reduced pressure of larger than 0.5 relative to the critical pressure of the anti-solvent fluid, the reduced pressure being a ratio of pressure expressed in atmospheres of the compressed anti-solvent fluid during the contacting to the critical pressure expressed in atmospheres of the compressed anti-solvent fluid.

44. The method of claim 43, wherein the compressed anti-solvent fluid, during the contacting step, is at a reduced temperature of larger than 0.95 relative to the critical temperature of the anti-solvent fluid, the reduced temperature being a ratio of temperature expressed in K of the compressed anti-solvent fluid during the contacting to the critical temperature expressed in K of the compressed anti-solvent fluid.

45. The method of claim 44, wherein the compressed anti-solvent fluid, during the contacting step, is at a reduced pressure of larger than 0.8 relative to the critical pressure of the anti-solvent fluid.

46. The method of claim 25, wherein the compressed anti-solvent fluid, during the contacting step, is in a supercritical state.

47. The method of claim 25, wherein the compressed anti-solvent fluid comprises compressed carbon dioxide.

48. The method of claim 25, wherein the compressed anti-solvent fluid consists essentially of only compressed carbon dioxide.

49. The method of claim 25, wherein during the contacting step, the feed solution is introduced into a flowing stream of the compressed anti-solvent fluid, the direction of flow of the feed solution, when introduced into the flowing stream of the compressed anti-solvent fluid, is at an angle of from 45° to 180° relative to the direction of flow of the compressed anti-solvent fluid.

50. The method of claim 25, wherein the multi-component particles have a degree of encapsulation of the insulin by the polymer of greater than 50 percent on a weight basis.

51. The method of claim 25, wherein the multi-component particles have a degree of encapsulation of the insulin by the polymer of greater than 70 percent on a weight basis.

52. The method of claim 25, wherein the biocompatible polymer includes a poly(lactic acid).

53. A method for making a particulate product containing insulin, the method comprising:

contacting, a feed solution containing insulin with a compressed anti-solvent fluid to precipitate particles containing insulin, the feed solution including the insulin in a cosolvent system, the cosolvent system comprising a first organic solvent and a second organic solvent that are mutually soluble, the first organic solvent and the second organic solvent not being the same; and separating the particles from the first organic solvent, the second organic solvent and the anti-solvent fluid;

wherein the concentration of insulin in the cosolvent system is smaller than 3 mg of insulin per milliliter of the feed solution.

54. The method of claim 53, wherein the concentration of insulin in the cosolvent system is in a range of from 0.3 to 3 mg of insulin per milliliter of the solution.

55. A method for making a particulate product containing insulin, the method comprising:

contacting a feed solution containing insulin with a compressed anti-solvent fluid to precipitate particles containing insulin, the feed solution including the insulin in a cosolvent system, the cosolvent system comprising a first organic solvent and a second organic solvent that are mutually soluble, the first organic solvent and the second organic solvent not being the same; and separating the particles from the first organic solvent, the second organic solvent and the anti-solvent fluid;

wherein the first organic solvent comprises a C1–C5 alkanol and the second organic solvent comprises methylene chloride.

* * * * *

UNITED STATES PATENT AND TRADEMARK OFFICE
CERTIFICATE OF CORRECTION

PATENT NO. : 6,761,909 B1
DATED : July 13, 2004
INVENTOR(S) : Etter

It is certified that error appears in the above-identified patent and that said Letters Patent is hereby corrected as shown below:

Column 25,
Line 9, delete "$_{45}$°", and insert therefor -- 45° --.
Line 23, after "contacting", delete -- , --.

Signed and Sealed this

Sixteenth Day of November, 2004

JON W. DUDAS
*Director of the United States Patent and Trademark Office*